(12) United States Patent
Galauner et al.

(10) Patent No.: US 7,513,781 B2
(45) Date of Patent: Apr. 7, 2009

(54) HEATING ELEMENT CONNECTOR ASSEMBLY WITH INSERT MOLDED STRIPS

(75) Inventors: Charles Galauner, Elburn, IL (US); Gregory Menn, Naperville, IL (US); Richard A. Nelson, Geneva, IL (US); Hazelton P. Avery, Batavia, IL (US); Timothy E. Purkis, Naperville, IL (US); Richard A. Faje, Darien, IL (US); Ryan D. Timmons, Mountain View, CA (US); Andrew J.G. Kelly, Redwood City, CA (US); Martin J. Wensley, Los Gatos, CA (US)

(73) Assignees: Molex Incorporated, Lisle, IL (US); Alexza Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 11/645,859

(22) Filed: Dec. 27, 2006

(65) Prior Publication Data
US 2008/0156325 A1    Jul. 3, 2008

(51) Int. Cl.
*H01R 12/00* (2006.01)
(52) U.S. Cl. .................. 439/70; 439/509
(58) Field of Classification Search .......... 439/70, 439/82, 509, 511, 751
See application file for complete search history.

(56) References Cited

U.S. PATENT DOCUMENTS

| | | | | |
|---|---|---|---|---|
| 3,846,734 | A | * | 11/1974 | Pauza et al. ............. 439/70 |
| 3,905,667 | A | * | 9/1975 | Crimmins et al. ........ 439/511 |
| 4,090,667 | A | * | 5/1978 | Crimmins ............... 439/189 |
| 4,097,113 | A | | 6/1978 | McKelvy |
| 4,645,943 | A | * | 2/1987 | Smith et al. ............. 307/150 |
| 4,735,217 | A | | 4/1988 | Gerth et al. |
| 4,819,665 | A | | 4/1989 | Roberts et al. |
| 4,883,428 | A | * | 11/1989 | Tonooka ................. 439/69 |
| 4,892,109 | A | | 1/1990 | Strubel |
| 4,894,015 | A | | 1/1990 | Stockero et al. |
| 4,917,119 | A | | 4/1990 | Potter et al. |
| 4,922,901 | A | | 5/1990 | Brooks et al. |

(Continued)

FOREIGN PATENT DOCUMENTS

DE    24 49 739    4/1979

(Continued)

OTHER PUBLICATIONS

International Search Report for PCT/US2006/049217.

*Primary Examiner*—Thanh-Tam T Le
(74) *Attorney, Agent, or Firm*—Thomas D. Paulius

(57) ABSTRACT

An improved heating element connector assembly includes an insulative, rectangular frame with a central opening, and a plurality of conductive terminals which are press fit into openings in the frame. The terminals are spaced apart from each other lengthwise of two opposing sidewalls of the frame, and pairs of terminals are aligned with each other between the two sidewalls. A plurality of conductive strips are held together in an assembly and the ends of the strips are interconnected along two spaced apart lines by carrier members that may be molded over the ends of the conductive strips. The carrier members extend down into cavities on the frame and terminals are pushed into the cavities to bear against the ends of the strips and effect an electrical connection between the terminals and the strips.

15 Claims, 7 Drawing Sheets

U.S. PATENT DOCUMENTS

| | | | |
|---|---|---|---|
| 4,935,624 A | 6/1990 | Henion et al. |
| 4,941,483 A | 7/1990 | Ridings et al. |
| 4,947,874 A | 8/1990 | Brooks et al. |
| 4,947,875 A | 8/1990 | Brooks et al. |
| 4,968,885 A | 11/1990 | Willoughby |
| 5,038,769 A | 8/1991 | Krauser |
| 5,060,671 A | 10/1991 | Counts et al. |
| 5,093,894 A | 3/1992 | Deevi et al. |
| 5,095,921 A | 3/1992 | Losee et al. |
| 5,099,861 A | 3/1992 | Clearman et al. |
| 5,135,009 A | 8/1992 | Mueller et al. |
| 5,144,962 A | 9/1992 | Counts et al. |
| 5,179,966 A | 1/1993 | Losee et al. |
| 5,224,498 A | 7/1993 | Deevi et al. |
| 5,226,411 A | 7/1993 | Levine |
| 5,269,327 A | 12/1993 | Counts et al. |
| 5,285,798 A | 2/1994 | Banerjee et al. |
| 5,286,218 A | 2/1994 | Sakurai et al. |
| 5,322,075 A | 6/1994 | Deevi et al. |
| 5,357,984 A | 10/1994 | Farrier et al. |
| 5,400,969 A | 3/1995 | Keene |
| 5,402,517 A | 3/1995 | Gillett et al. |
| 5,408,574 A | 4/1995 | Deevi et al. |
| 5,456,247 A | 10/1995 | Shilling et al. |
| 5,479,948 A | 1/1996 | Counts et al. |
| 5,505,214 A | 4/1996 | Collins et al. |
| 5,537,507 A | 7/1996 | Mariner et al. |
| 5,538,020 A | 7/1996 | Farrier et al. |
| 5,565,148 A | 10/1996 | Pendergrass |
| 5,577,156 A | 11/1996 | Costello |
| 5,591,409 A | 1/1997 | Watkins |
| 5,593,792 A | 1/1997 | Farrier et al. |
| 5,613,504 A | 3/1997 | Collins et al. |
| 5,613,505 A | 3/1997 | Campbell et al. |
| 5,666,977 A | 9/1997 | Higgins et al. |
| 5,735,263 A | 4/1998 | Rubsamen et al. |
| 5,819,756 A | 10/1998 | Mierlordt |
| 5,865,185 A | 2/1999 | Collins et al. |
| 5,904,900 A | 5/1999 | Bleuse et al. |
| 6,004,516 A | 12/1999 | Rasouli et al. |
| 6,053,176 A | 4/2000 | Adams et al. |
| 6,071,152 A * | 6/2000 | Achammer et al. ...... 439/733.1 |
| 6,085,026 A | 7/2000 | Hammons et al. |
| 6,095,153 A | 8/2000 | Kessler et al. |
| 6,102,036 A | 8/2000 | Slutsky et al. |
| 6,131,570 A | 10/2000 | Schuster et al. |
| 6,155,268 A | 12/2000 | Takeuchi |
| 6,158,431 A | 12/2000 | Poole |
| 6,178,969 B1 | 1/2001 | St. Charles |
| 6,234,167 B1 | 5/2001 | Cox et al. |
| 6,250,301 B1 | 6/2001 | Pate |
| 6,263,872 B1 | 7/2001 | Schuster et al. |
| 6,309,986 B1 | 10/2001 | Flashinski et al. |
| 6,312,296 B1 * | 11/2001 | Jones .................. 439/751 |
| 6,325,475 B1 | 12/2001 | Hayes et al. |
| 6,328,033 B1 | 12/2001 | Avrahami |
| 6,390,453 B1 | 5/2002 | Frederickson et al. |
| 6,491,233 B2 | 12/2002 | Nichols |
| 6,501,052 B2 | 12/2002 | Cox et al. |
| 6,516,796 B1 | 2/2003 | Cox et al. |
| 6,526,969 B2 | 3/2003 | Nilsson et al. |
| 6,547,607 B2 | 4/2003 | Moll et al. |
| 6,557,552 B1 | 5/2003 | Cox et al. |
| 6,561,186 B2 | 5/2003 | Casper et al. |
| 6,568,390 B2 | 5/2003 | Nichols et al. |
| 6,648,950 B2 | 11/2003 | Lee et al. |
| 6,671,945 B2 | 1/2004 | Gerber et al. |
| 6,680,668 B2 | 1/2004 | Gerber et al. |
| 6,681,769 B2 | 1/2004 | Sprinkel et al. |
| 6,681,998 B2 | 1/2004 | Sharpe et al. |
| 6,684,880 B2 | 2/2004 | Trueba et al. |
| 6,688,313 B2 | 2/2004 | Wrenn et al. |
| 6,694,975 B2 | 2/2004 | Schuster et al. |
| 6,701,921 B2 | 3/2004 | Sprinkel et al. |
| 6,701,922 B2 | 3/2004 | Hindle et al. |
| 6,715,487 B2 | 4/2004 | Nichols et al. |
| 6,728,478 B2 | 4/2004 | Cox et al. |
| 2001/0042546 A1 | 11/2001 | Umeda et al. |
| 2002/0078955 A1 | 6/2002 | Nichols et al. |
| 2002/0097139 A1 | 7/2002 | Gerber et al. |
| 2002/0117175 A1 | 8/2002 | Kottayil et al. |
| 2003/0015196 A1 | 1/2003 | Hodges et al. |
| 2003/0015197 A1 | 1/2003 | Hale et al. |
| 2003/0033055 A1 | 2/2003 | McRae et al. |
| 2003/0049025 A1 | 3/2003 | Neumann et al. |
| 2003/0051728 A1 | 3/2003 | Lloyd et al. |
| 2003/0062042 A1 | 4/2003 | Wensley et al. |
| 2003/0106551 A1 | 6/2003 | Sprinkel et al. |
| 2003/0121906 A1 | 7/2003 | Abbott et al. |
| 2003/0132219 A1 | 7/2003 | Cox et al. |
| 2003/0156829 A1 | 8/2003 | Cox et al. |
| 2003/0209240 A1 | 11/2003 | Hale et al. |
| 2004/0035409 A1 | 2/2004 | Harwig et al. |
| 2004/0055504 A1 | 3/2004 | Lee et al. |
| 2004/0081624 A1 | 4/2004 | Nguyen et al. |
| 2004/0099266 A1 | 5/2004 | Cross et al. |
| 2005/0268911 A1 | 12/2005 | Cross et al. |
| 2007/0155255 A1 * | 7/2007 | Galauner et al. ............ 439/891 |

FOREIGN PATENT DOCUMENTS

| | | |
|---|---|---|
| DE | 32 45 746 | 6/1984 |
| DE | 101 00 189 | 7/2001 |
| DE | 103 21 184 | 12/2004 |
| GB | 732905 | 6/1955 |
| GB | 1 567 523 | 5/1977 |
| WO | WO 94/09842 A1 | 5/1994 |
| WO | WO 02/051466 A2 | 7/2002 |
| WO | WO 02/051469 A2 | 7/2002 |
| WO | WO 02/098496 A1 | 12/2002 |
| WO | WO 03/037412 A2 | 5/2003 |
| WO | WO 03/049535 A1 | 6/2003 |

* cited by examiner

HEATING ELEMENT CONNECTOR ASSEMBLY WITH INSERT MOLDED STRIPS

REFERENCE TO RELATED APPLICATIONS

There are no related applications at this time.

BACKGROUND OF THE INVENTION

The present invention relates generally to connectors, and more particularly to connector assemblies used in heating assemblies.

Heating elements are used in a variety of applications. Recently, heating elements have been used in drug delivery systems. In such systems, a heating element is provided as an assembly that has a plurality of individual conductive members held upon a frame. The individual elements are coated with a drug, so that when the elements are energized and heated to a specific temperature, the drug is vaporized and a patient can readily and easily inhale the drug.

Current heating element assemblies use a frame and a series of conductive terminals that are mounted to a circuit board. Conductive foil strips are soldered to the circuit board in order to create electrical continuity. This manner of construction is expensive and difficult.

Accordingly, the present invention is directed to a heating element connector structure of simplified and reliable construction that has a low cost of manufacture.

SUMMARY OF THE INVENTION

Accordingly, it is a general object of the present invention to provide a new and improved heating element connector assembly of simplified construction and reduced cost.

It is another object of the present invention to provide a reliable electrical contact structure for use in a heating element assembly that utilizes only mechanical connections rather than soldered connections and in which the mechanical connections serve to connect together individual conductive strips to conductive terminals.

Yet another object of the present invention is to provide an improved heating element connector assembly including an insulative, rectangular frame with a central opening, a plurality of conductive terminals disposed in the frame, the terminals being spaced apart from each other lengthwise of two opposing sidewalls of the frame, the terminal further being aligned with each other as between the two sidewalls, and a plurality of conductive strips extending across the frame opening and interconnecting pairs of terminals together, the terminals including compliant pin tail portions for receipt by corresponding holes form in a circuit board associated with the assembly.

Yet a still further object of the present invention is to provide a heating element connector assembly of the type described above, wherein the terminals include contact portions in the form of out of plane bends, which contact portions may be inserted into engagement slots of the assembly in order to create bearing, or frictional, contact with the conductive strips.

In accordance with the present invention, an insulative frame is provided in the form of an open rectangle. The frame has two side walls that are interconnected by a pair of end walls, the end walls preferably being of a shorter length than the side walls to give the frame a rectangular configuration. The frame side walls have a plurality of terminal-receiving cavities disposed in them. These cavities are arranged in an array that runs lengthwise of each frame side wall, and each such cavity only receives a single terminal. The terminals are further aligned together across the frame opening in pairs of terminals.

The assembly also includes a plurality of conductive strips that extend across the frame opening and which interconnect aligned pairs of the terminals together. These conductive strips are preferably formed from a conductive foil, and the foil is further preferably formed with an upward bow in it so that the central portions of the strips rise to a level above the top of the frame. The strips are insert molded into two carrier members that also extend lengthwise of the frame. These carrier members fit into openings formed in the frame sidewalls as a single assembly and terminals are then inserted into cavities that communicate with portions.

The terminals may be inserted into cavities in the frame, and they have a vertical extent, with a body portion that runs generally horizontally and a tail portion in the form of a compliant pin. The terminals include contact portions at ends of the terminal opposite to the tail portions. The contact portions are disposed preferably above the body portions when the terminals are arranged in their vertical orientation, and the contact portions include at least one bend disposed therein that extends out of the plane of the terminal. This bend defines a contact surface of the contact portion.

The ends of the conductive strips are supported within the carriers and they are molded in place within the carriers. The strip ends are supported in a position so that the terminal bends will impinge upon them when the terminals are inserted into the cavities in the frame of the assembly.

The terminal body portions have flat opposing ends. The bottom ends form surfaces that may be used to insert the terminals into their receiving cavities and the top ends form stop surfaces that limit the distance the terminals may be inserted into the frame cavities.

These and other objects, features and advantages of the present invention will be clearly understood through a consideration of the following detailed description.

BRIEF DESCRIPTION OF THE DRAWINGS

In the course of this detailed description, the reference will be frequently made to the attached drawings in which.

DETAILED DESCRIPTION OF THE PREFERRED EMBODIMENTS

Figure 1:
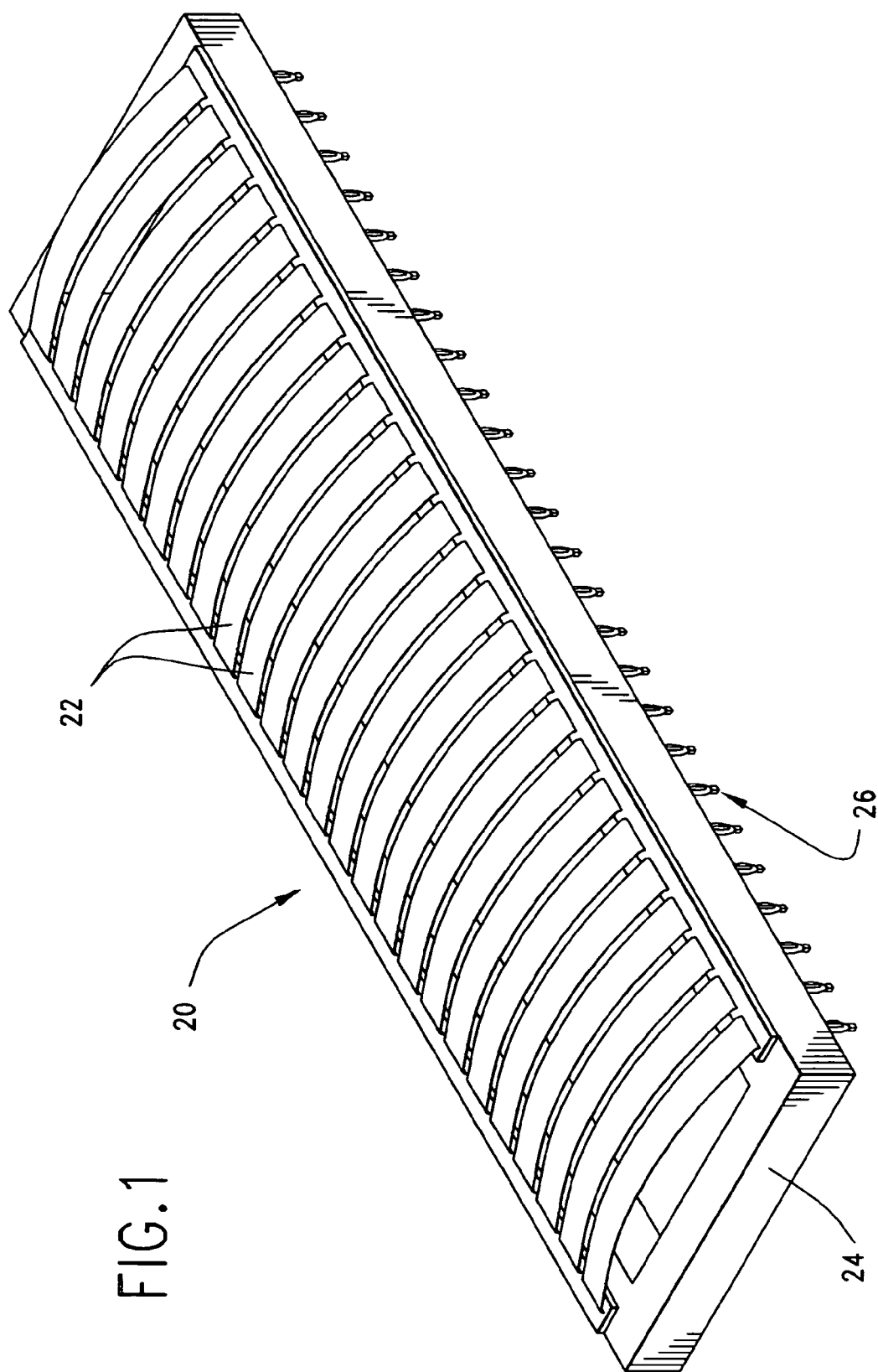
FIG. 1 is a perspective view of a heating element connector assembly constructed in accordance with the principles of the present invention.

FIG. 1 illustrates a heating element connector assembly 20 that is constructed in accordance with the principles of the present invention. The assembly 20 is comprised of a plurality of individual conductive strips 22 that are supported by a frame 24, which is intended to be mounted to a circuit board (not shown). The individual strips 22 are preferably formed from a conductive material such as a metal foil, or the like.

The strips 22 each define an individual heating element of the assembly 20, which can be heated when a current is passed through the strip 22. In this regards, the strips 22 are supported by an insulative frame 24, and the frame 24 contains a plurality of conductive terminals 26. Each terminal 26, as explained in greater detail to follow, has a contact portion 27 that makes contact with the strips 22, and a tail portion 29 that extends out from the frame 24 and which provides a means of connecting the individual strips 22 to heating circuits on the circuit board 25 which provide a pass through current to energize the strips 22. The terminal tail portions 29 are preferably received within plated through holes formed in the circuit board.

Figure 3:
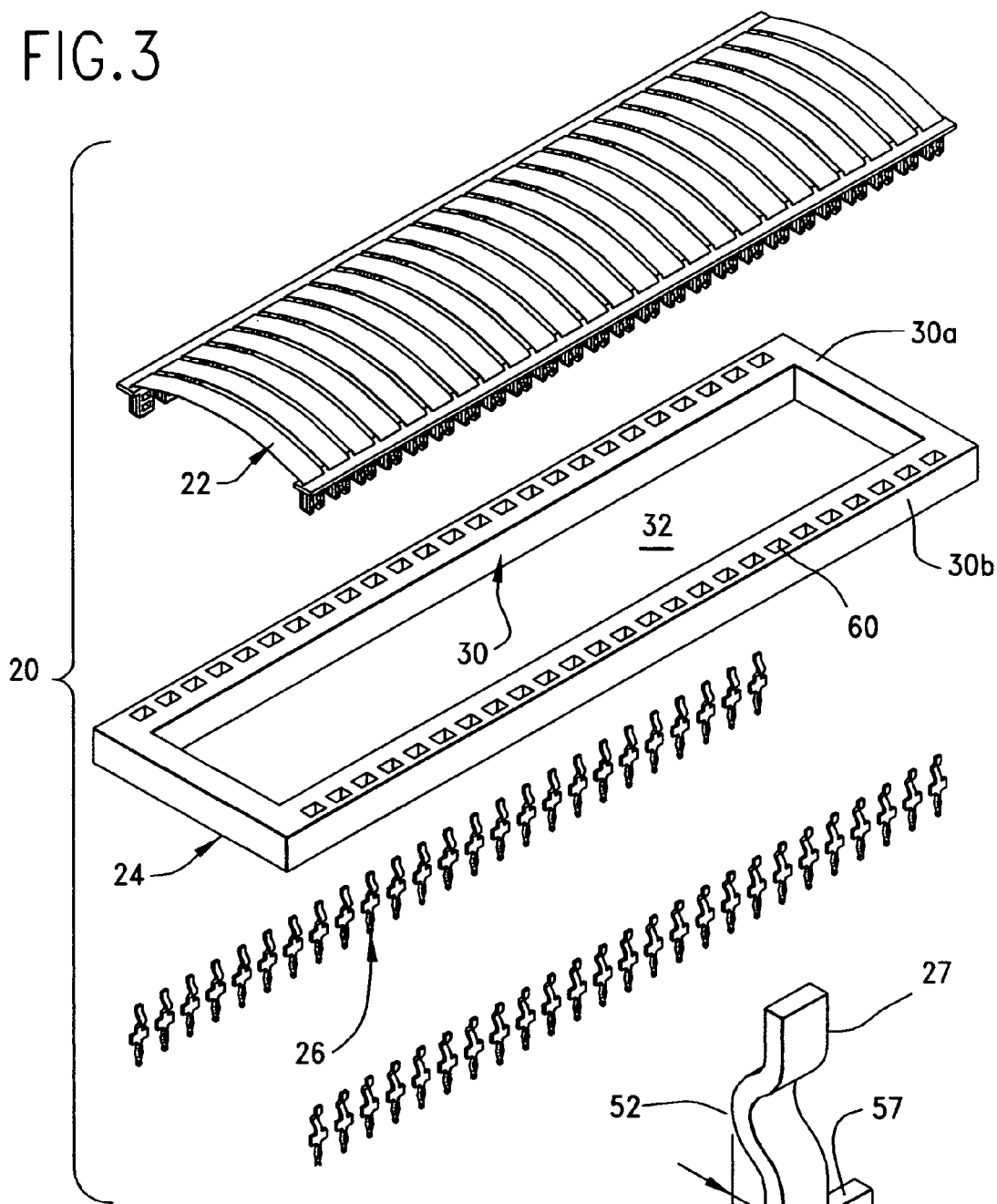
FIG. 3 is an exploded view of the heating element connector assembly of FIG. 1.
Figure 4:
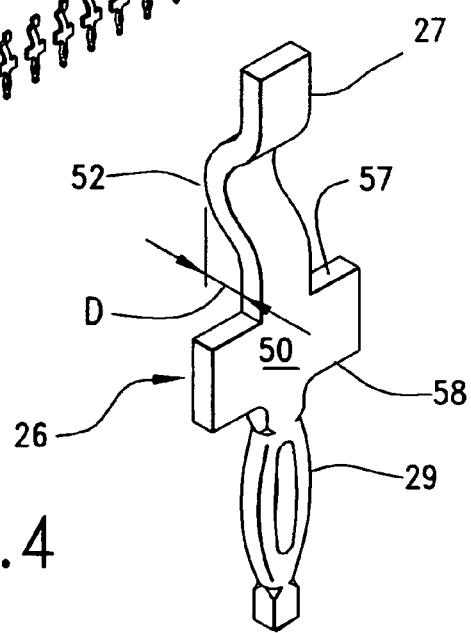
FIG. 4 is a perspective view of a terminal utilized in the heating element connector assembly of FIG. 1.
Figure 5:
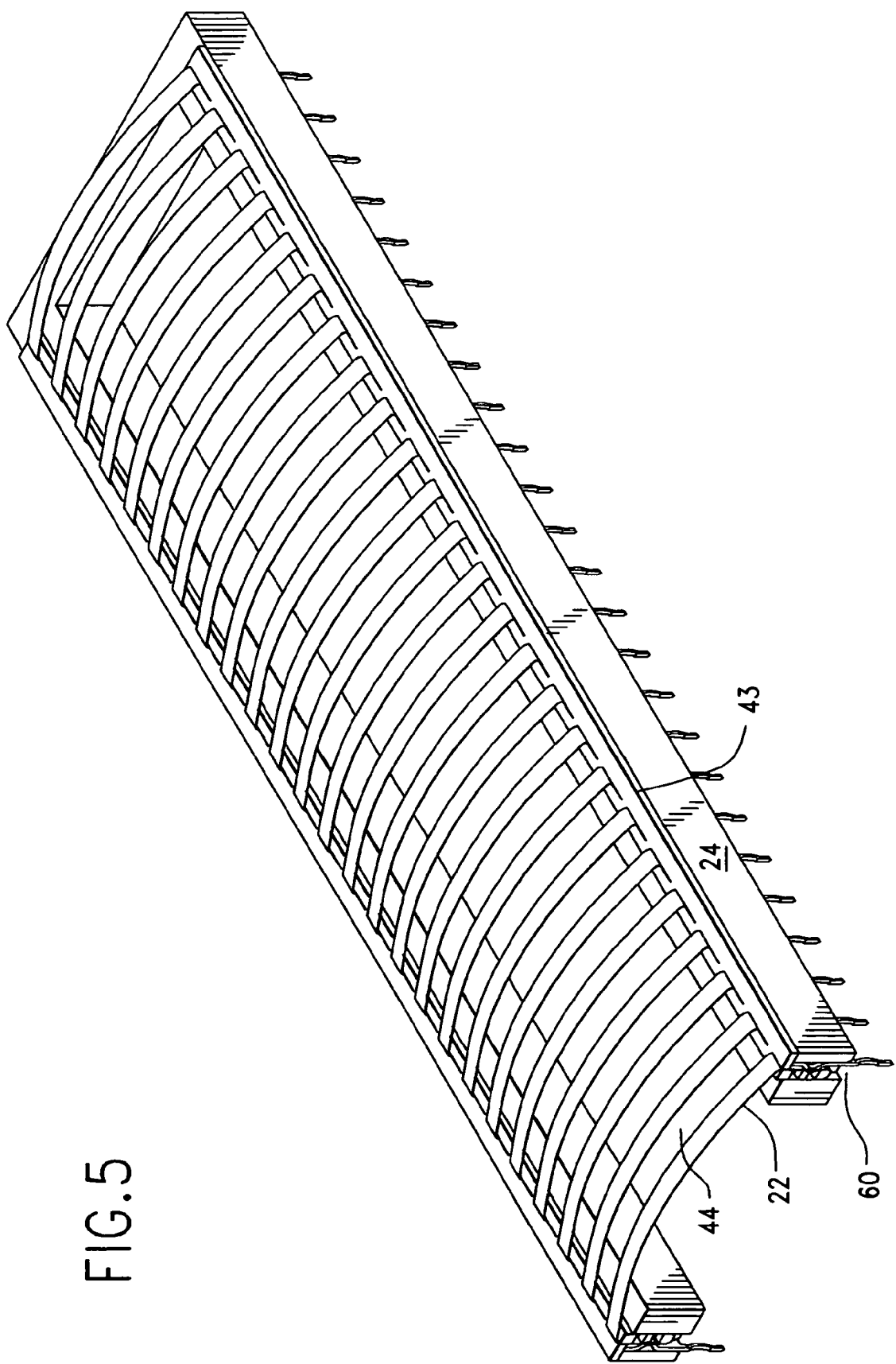
FIG. 5 is a perspective view of the heating element assembly, with the frame portion thereof illustrated partially in section.
Figure 6:
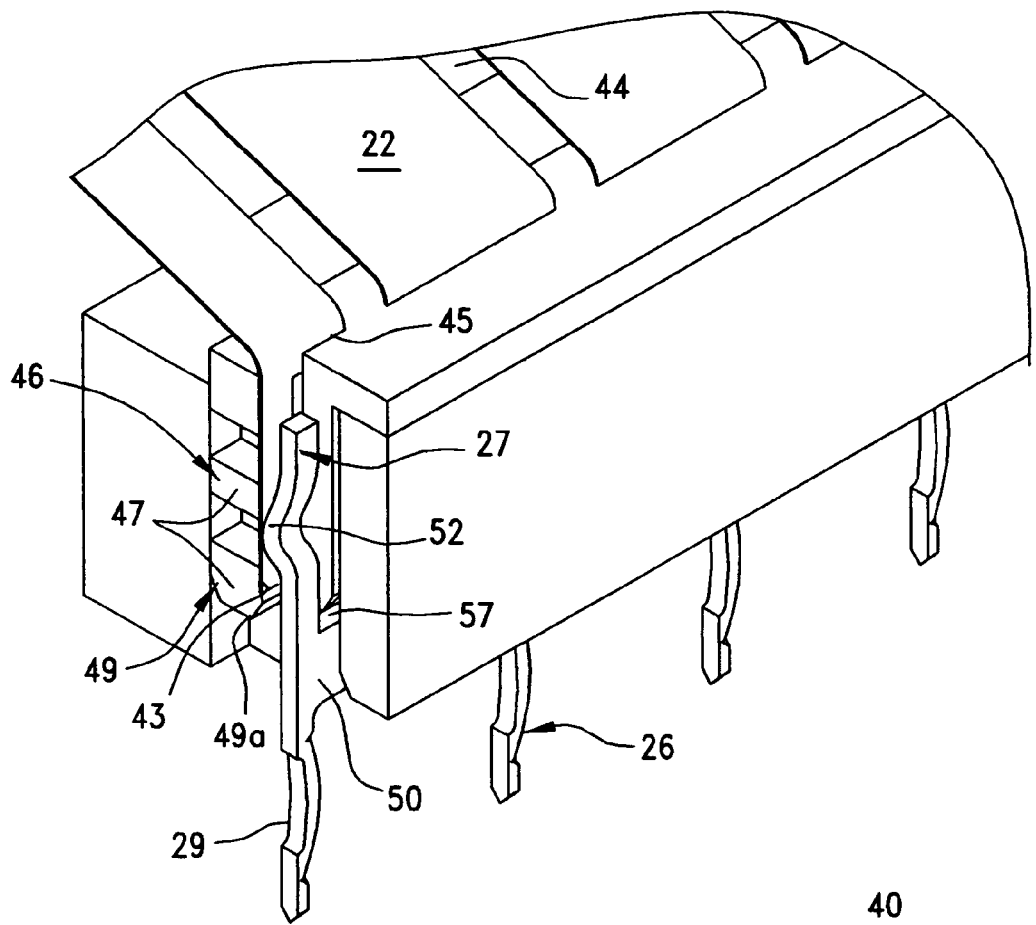
FIG. 6 is an enlarged end view of a potion of FIG. 5.

FIG. 3 illustrates the assembly 20 in exploded fashion, while FIG. 4 illustrates the terminal 26. As shown, the frame 24 is rectangular in shape having four sidewalls 30 that cooperatively define a central opening 32. The frame sidewalls 30 include end walls 30a and longitudinal sidewalls 30b which in most instances will have a length longer than that of the end walls 30a in order to give the assembly its rectangular configuration shown. The sidewalls 30b are spaced apart from each other and the opening 32 of the frame is spanned by the conductive strips 22.

The strips 22 are formed as part of an overall carrier strip or assembly 40 that is also configured to match the configuration of the frame 24 and which is shown as rectangular in the drawings. The carrier strip 40 has a pair of carrier members 42 formed along opposite ends 43 of the conductive strips 22. The individual strips 22 are separated from each other by intervening spaces which appear as slots 44 that extend transversely to a longitudinal axis of the assembly 20. The carrier members 22 each have a cap portion 45 that extends horizontally and which is molded in place around the conductive strips 22. A body portion 46 extends downwardly from the cap portions 45 and this body portion 46 encompasses the ends 43 of individual conductive strips 22. The body portions 46 can be seen to include one or more ribs 47 that are disposed in the inner side of the carrier member body portions 45. These ribs 47 provide a reaction and pressing surface for the terminals 26 as explained in greater detail below.

One of the terminals 26 is shown illustrated in FIG. 4, and it can seen to extend generally vertically, and the terminals include a wide body portion 50. The terminal contact portions 29 can be see in FIG. 4 to rise up from its associated terminal body portion 50. The contact portions 29 include a bend 52 that extends outwardly toward the frame opening 32 and out of the plane of the terminal 26. The extent is shown in FIG. 4 as distance D.

Figure 2:
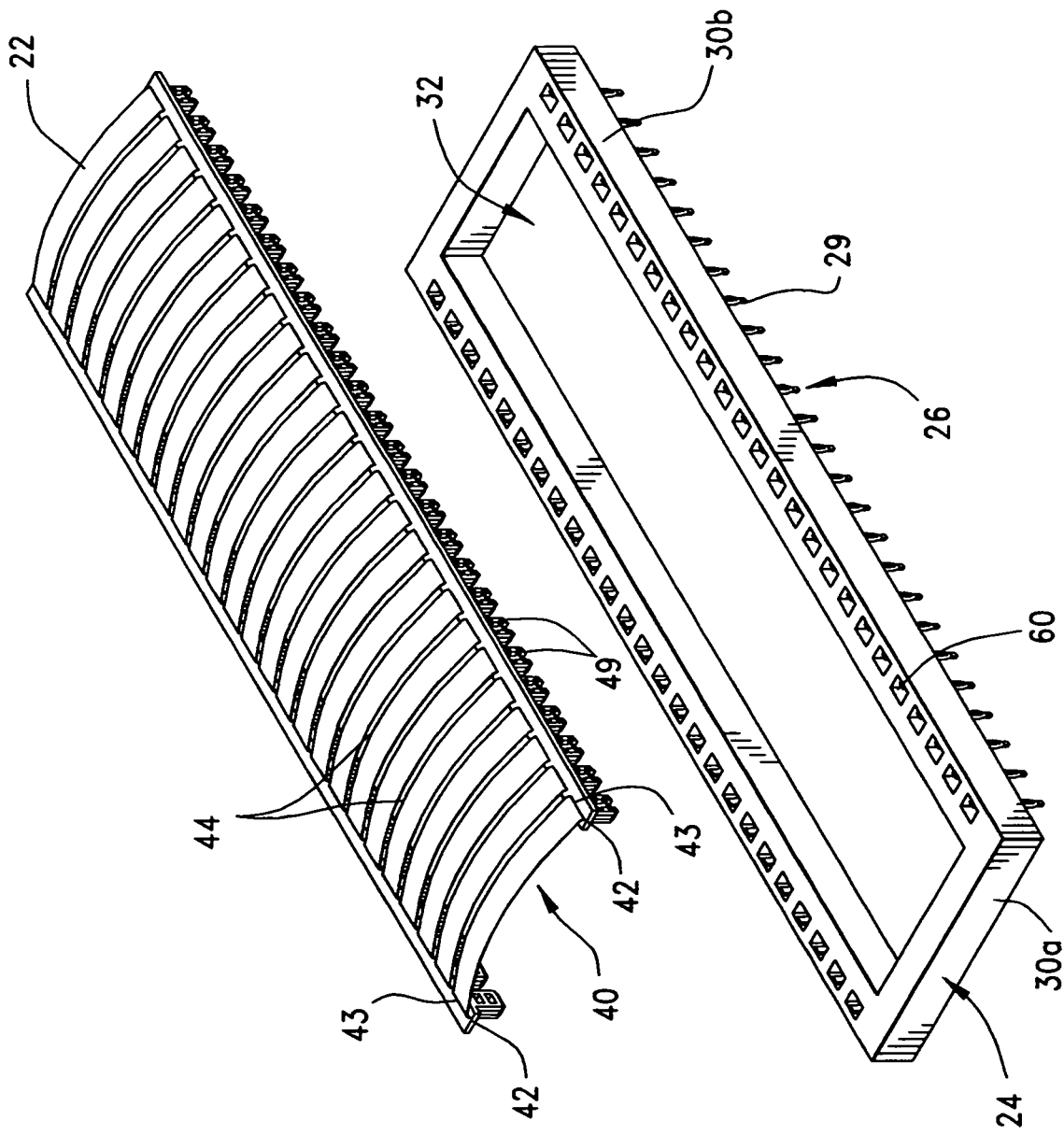
FIG. 2 is the same view as FIG. 1, but with the heating element assembly removed from its frame.

The terminals 26 are received in cavities 60 of the frame 24 that are best shown in FIGS. 2 & 3, and which can be seen to receive individual insert portions 49 that serve to hold the ends 43 of the conductive strips 22 and which receive portions of the terminal 26 therein.

Figure 10:
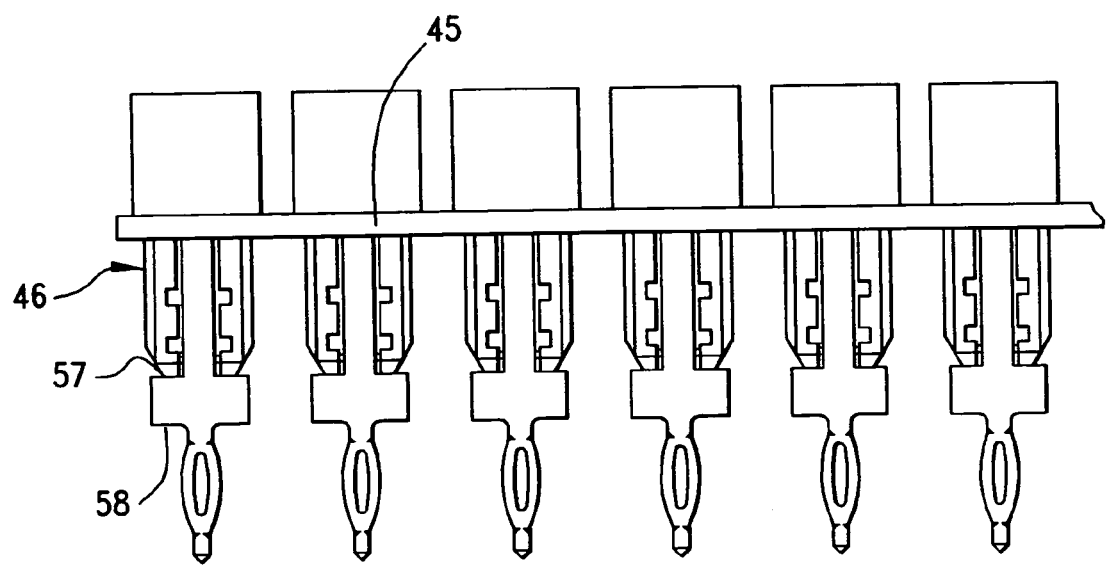

The terminal body portions 50 also can be seen to include opposing flat ends 57, 58. The bottom ends form first reaction surfaces 58 against which a tool may press in order to insert the terminals 26 into the frame cavities 60. The top flat ends 57 of the terminals 26 form stop surfaces which bear against the bottom edges 49a of the individual inserts 49. This is shown in FIG. 10.

Figure 7:
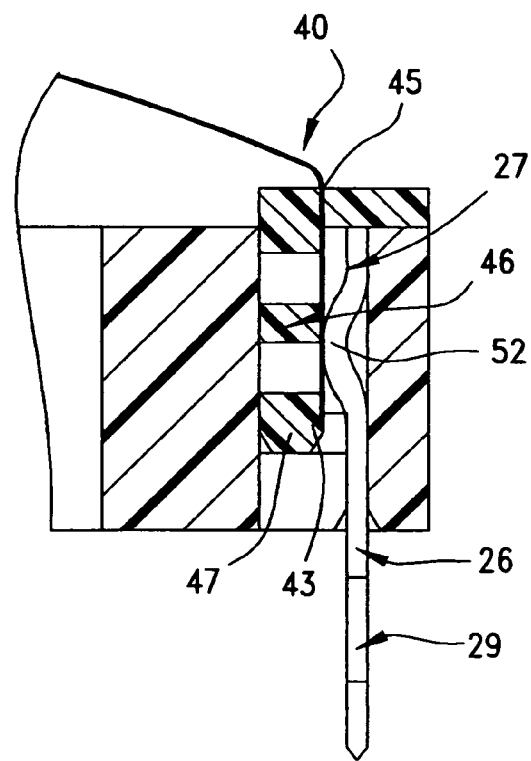
FIG. 7 is a end elevational view of the end of the assembly of FIG. 5, illustrating the assembly in section: and, FIG. 8 is a detail perspective view of the carrier strips of the assembly with three terminals in place in contact with the conductive strips.
Figure 8:
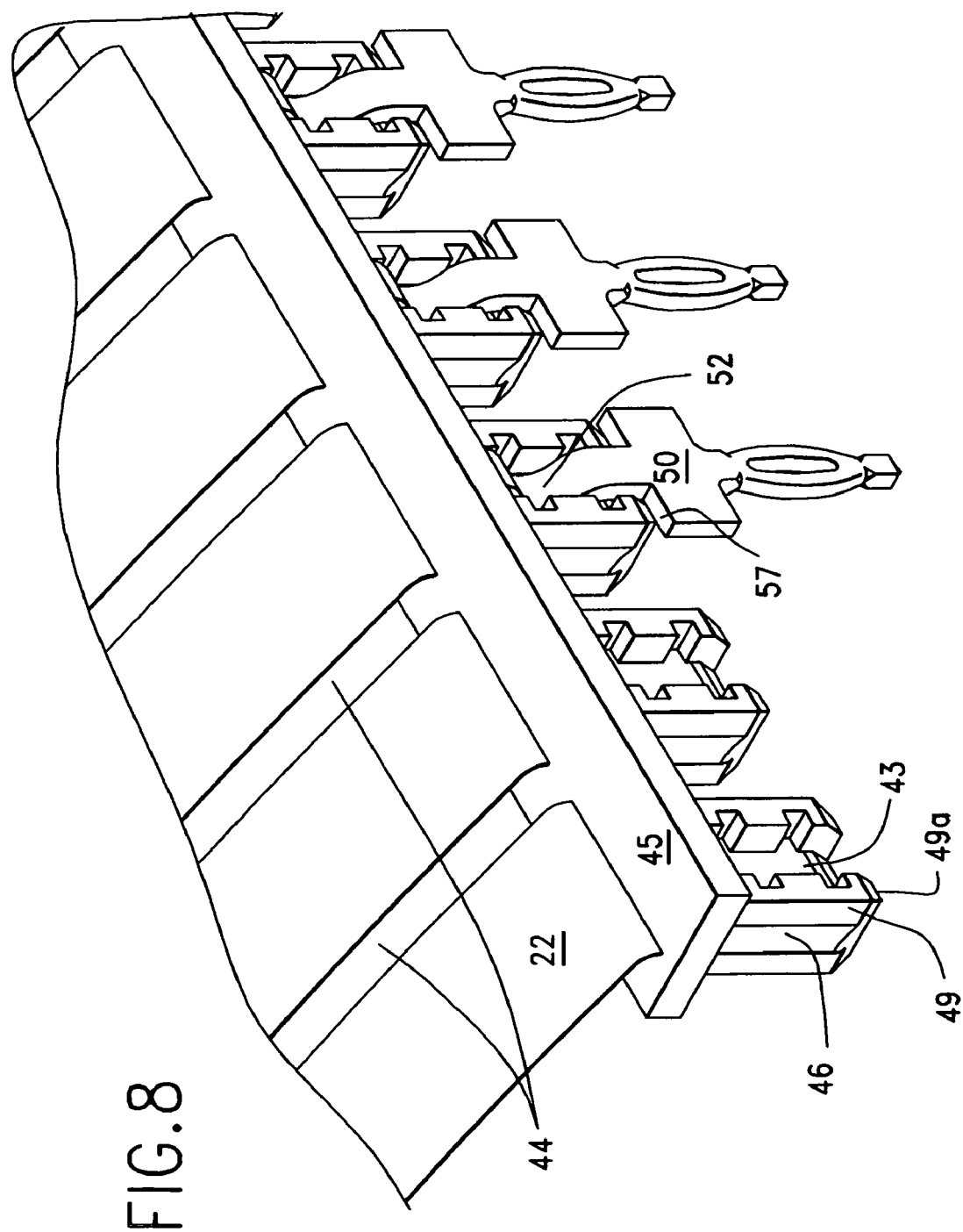
Figure 9:
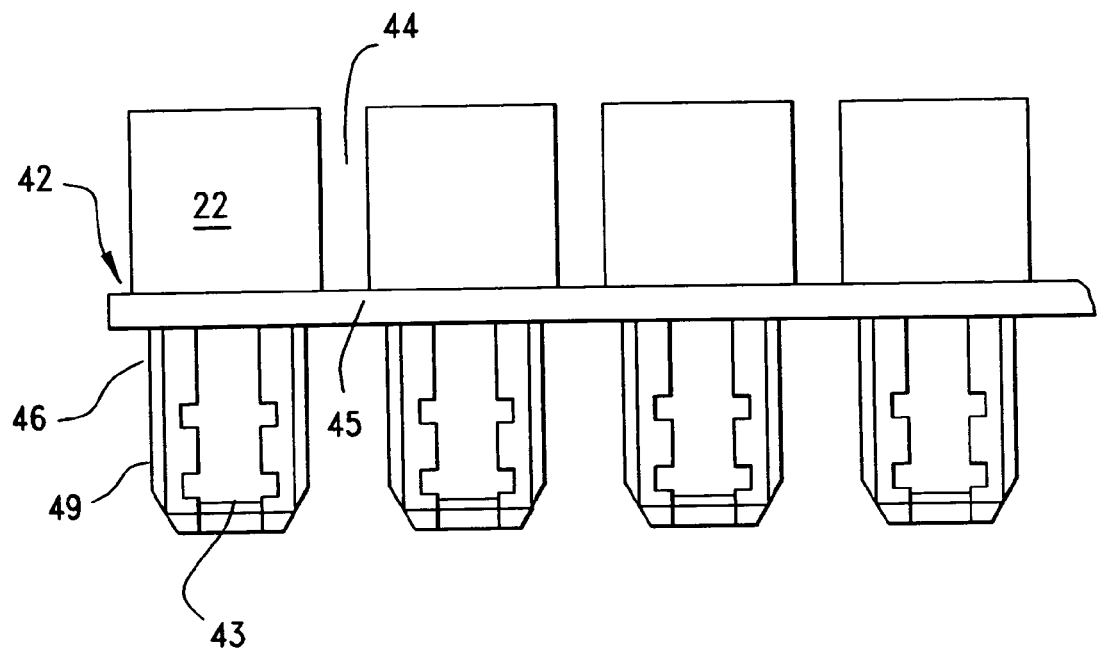
FIG. 9 is a side elevational view of a portion of the carrier strip illustrating the ends of the conductive strips in place; and, FIG. 10 is the same view as FIG. 9, but with terminal in place within the carrier strip foil holding portions.

The ends 43 of the conductive strips 22 are held in place in the carrier members 42 and the ribs 47 of the body portions 46 thereof support the strip ends 43. These ribs 47 occupy only a portion of the frame cavities 60, shown in FIG. 7 as about one-half the width of the cavity 60. The terminal contact portion 27, particularly the bend 52 will occupy the remaining space in the cavity 60. This bend provides an interference fit with the conductive strip 22 and provides a reliable mechanical and electrical connector that dispenses with the need for a soldered joint.

While the preferred embodiment of the invention have been shown and described, it will be apparent to those skilled in the art that changes and modifications may be made therein without departing from the spirit of the invention, the scope of which is defined by the appended claims.

The invention claimed is:

1. An improved connector assembly, the assembly comprising:
   an insulative, rectangular frame, the frame including a pair of lengthwise side walls that are interconnected together by widthwise end walls, the side walls and end walls cooperatively defining a central opening of the frame, said frame includes a plurality of cavities;
   a plurality of conductive terminals supported by said frame, the terminals being spaced apart from each other in an array that runs lengthwise in each of said two sidewalls, said terminals being aligned with each other in pairs in said two sidewalls across the frame opening, said terminals including tail and contact portions disposed at opposite ends thereof, the terminal tail portions including compliant pin tail portions for receipt by corresponding holes in a circuit board and the terminal contact portions including bends extending outwardly; and,
   a plurality of conductive strips extending across the frame opening and interconnecting the pairs of terminals together, said conductive strips being held together as a group by a pair of carrier members, free ends of individual conductive strips being held in position by the carrier members, said carrier members including individual body portions, each of which retains a conductive strip free end and a terminal, each carrier member body portion and a terminal being received in a single frame cavity.

2. The connector assembly of claim 1, wherein said terminal body portions have a width that is greater than corresponding widths of any one of said terminal tail or contact portions.

3. The connector assembly of claim 1, wherein each of said terminals includes a body portion interconnecting said tail and contact portions together, and the terminal body portions press against said conductive strip free ends.

4. The connector assembly of claim 1, wherein said terminal body portions each include a pair of flat surfaces flanking said contact portions, the flat surface defining stop surfaces which bear against ends of said carrier member body portions.

5. The connector assembly of claim 1, wherein said conductive strips are formed from a conductive foil and exhibit a crown with respect to said frame side walls.

6. A connector assembly, the assembly comprising:
   an insulative frame, the frame including a pair of lengthwise side walls that are interconnected together by widthwise end walls, the side walls and end walls cooperatively defining a central opening of said frame;

a plurality of conductive terminals supported by said frame, the terminals being spaced apart from each other in an array that runs lengthwise in each of said two sidewalls, said terminals being aligned with each other in pairs in said two sidewalls across the frame opening, each of said terminals including tail and contact portions disposed at opposite ends thereof, the terminal tail portions including compliant pin tail portions for receipt by corresponding holes in a circuit board; and a plurality of conductive strips extending across the frame opening and interconnecting the pairs of terminals together, the conductive strips having opposing end portions;

wherein the terminal contact portions engaging the end portions of said conductive strips within a retainer system that secures said terminals and said conductive strip end portions together, the retainer system mounting on said frame, wherein said conductive strips are held together as a group by a pair of carrier members of the retainer system, said opposing end portions of individual conductive strips being held in position by the carrier members, said carrier members including individual body portions, each of which retains a conductive strip end portion, and wherein said frame includes a plurality of cavities, each of the cavities receiving a single terminal and a single one of the carrier member body portions in an interference fit therewithin.

7. The connector assembly of claim 6, wherein each of said terminals generally lies along a plane and includes a body portion interconnecting said tail and contact portions together, and the terminal contact portions include contact surfaces that extend out of the plane of said terminals and toward said opposing end portions of said conductive strips.

8. The connector assembly of claim 7, wherein each said terminal body portions have a width that is greater than the width of said tail portion and said contact portion of said terminal.

9. The connector assembly of claim 6, wherein each of said terminals includes a body portion interconnecting said tail and contact portions together, and the terminal body portions include the terminal contact portions and press against said conductive strip opposing end portions.

10. The connector assembly of claim 6, wherein said terminal body portions each include a pair of flat surfaces flanking said contact portions, the flat surface defining stop surfaces which bear against ends of said carrier member body portions.

11. The connector assembly of claim 6, wherein said carrier members have extending cap portions molded in place around said conductive strips opposing end portions.

12. The connector assembly of claim 6, wherein said terminal contact portions includes bends that extend outwardly with respect to said terminals.

13. The connector assembly of claim 6, wherein said body portions of the carrier members include ribs that engage the end portions of the conductive strips, and said conductive strip end portions are positioned between the ribs and said terminals.

14. The connector assembly of claim 6, wherein said conductive strips are formed from a conductive foil and exhibit a crown with respect to said frame side walls, said crown being defined by said conductive strips being spaced away from said frame side walls.

15. The connector assembly of claim 6, wherein said conductive strips comprise heating elements that have current responsive properties and that elevate in temperature when electric current is passed therethrough.

\* \* \* \* \*

UNITED STATES PATENT AND TRADEMARK OFFICE
CERTIFICATE OF CORRECTION

| | | |
|---|---|---|
| PATENT NO. | : 7,513,781 B2 | Page 1 of 1 |
| APPLICATION NO. | : 11/645859 | |
| DATED | : April 7, 2009 | |
| INVENTOR(S) | : Charles Galauner et al. | |

It is certified that error appears in the above-identified patent and that said Letters Patent is hereby corrected as shown below:

Insert immediately after the Title of the Invention

--This invention was made with Government support under Grant No. R43 HL073537, awarded by the National Institutes of Health. The Government has certain rights in the invention.--.

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,513,781 B2 | Page 1 of 1 |
| APPLICATION NO. | : 11/645859 | |
| DATED | : April 7, 2009 | |
| INVENTOR(S) | : Charles Galauner et al. | |

It is certified that error appears in the above-identified patent and that said Letters Patent is hereby corrected as shown below:

Column 1, line 3, Insert immediately after the Title of the Invention

--This invention was made with Government support under Grant No. R43 HL073537, awarded by the National Institutes of Health. The Government has certain rights in the invention.--.

This certificate supersedes the Certificate of Correction issued May 11, 2010.

Signed and Sealed this

Fifteenth Day of June, 2010

David J. Kappos
*Director of the United States Patent and Trademark Office*